United States Patent [19]

Bristow et al.

[11] Patent Number: 4,988,499
[45] Date of Patent: Jan. 29, 1991

[54] ORAL COMPOSITIONS

[75] Inventors: Neil J. Bristow, New South Wales, Australia; Peter Carter, Burton; Bryony E. Coulson, Port Sunlight; Michael A. Trevethan, Bebington, all of Great Britain

[73] Assignee: Unilever Patent Holdings, B.V., Rotterdam, Netherlands

[21] Appl. No.: 354,659

[22] Filed: May 19, 1989

[30] Foreign Application Priority Data

May 19, 1988 [GB] United Kingdom ............... 8811828

[51] Int. Cl.$^5$ ........................... A61K 9/16; A61K 9/18
[52] U.S. Cl. .......................................... 424/52; 424/57
[58] Field of Search ............................. 424/49, 52, 57

[56] References Cited

U.S. PATENT DOCUMENTS

| | | | |
|---|---|---|---|
| 4,327,079 | 4/1982 | Aoki | 424/57 |
| 4,342,741 | 8/1982 | Aoki | 424/57 |
| 4,634,589 | 1/1987 | Scheller | 424/57 |
| 4,684,518 | 8/1987 | Parran et al. | 424/52 |
| 4,923,683 | 5/1990 | Sakuma et al. | 424/52 |

FOREIGN PATENT DOCUMENTS 999238 11/1976 Canada.
0342380 4/1989 European Pat. Off..
1586915 3/1981 United Kingdom.

OTHER PUBLICATIONS

The Relationship between Anticaries Activity of Monofluorophosphate Dentifrices and Their Performances in Laboratory Tests, S. A. Duke, G. C. Forward; Caries Res. 19:284–288 (1985).
Improving the Performance of Sodium Monofluorophosphate to Protect Enamel Against Acid, G. C. Forward, M. A. Bell and S. A. Duke; Caries Res. 13: 61–67 (1979).
European Search Report on EPA No. EP 89201202.2.
Berndt et al. CA. 77:835V (1972).
Ingram C. A. 80:102m (1974).
Forward CA. 90:162133f (1979).
Duke C.A. 102:215149r (1985).

*Primary Examiner*—Shep K. Rose
*Attorney, Agent, or Firm*—Milton L. Honig

[57] ABSTRACT

The invention relates to oral compositions for combating dental caries. The compositions comprise a fluorine-containing anti-caries agent such as sodium fluoride or sodium monofluorophosphate and a particulate hydroxyapatite as abrasive. These ingredients are surprisingly compatible in that there is a reduced loss of available fluoride upon storage.

4 Claims, No Drawings

ORAL COMPOSITIONS

BACKGROUND OF THE INVENTION

This invention relates to oral compositions, more particularly compositions for combating dental caries.

THE RELATED ART

In the dental caries process acid formed in the materials covering the tooth surface attacks the mineral hydroxyapatite of which tooth enamel is mainly composed resulting in a loss of calcium ions. This demineralisation of the tooth mineral can be countered by the action of fluoride which reacts with tooth mineral replacing some of the hydroxyl ions by fluoride ions producing fluoroapatite which has a greater resistance to acid attack. Other mechanisms are also believed to play a part in the anti-caries action of fluorides.

It has long been known to include fluorine-containing compounds in dentifrices as anti-caries agents, and it has been established that these compounds are effective to reduce the incidence of dental caries. Those compounds most commonly used today are sodium fluoride and sodium monofluorophosphate. Other examples of known fluorine-containing anti-caries agents are stannous fluoride, amine fluorides and other fluoride-ion sources e.g. as described in U.S. Pat. No. 4,684,518 (Parran et al.).

In the formulation of so-called fluoride dentifrices it is recognized by those skilled in the art that during the period of time between manufacture of the dentifrice and use by the consumer, there must be no undue loss of availability of the fluoride active component due to reaction with other ingredients of the dentifrice. Of particular importance in this respect is the choice of a particulate abrasive component. Substantial loss of available fluorine through interaction with the abrasive must be avoided if the dentifrice is to be effective in inhibiting dental caries. A number of particulate abrasive agents are known to those skilled in the art to be compatible with selected fluoridating agents.

Among the large number of materials that have been suggested for use as the abrasive cleaning agent of dentifrices is at least one which itself is said to be effective in bringing about a remineralisation of tooth mineral. Such abrasive is one which is actually composed of the same material as the tooth, namely hydroxyapatite. Reference to the use of finely-divided hydroxyapatite as a component of a dentifrice is found in a number of patents. One such patent is CA-A-999 238 (Kodderman) which describes and claims an oral or dental preparation containing 5 to 90% by weight of a finely divided hydroxyapatite having an average particle size of less than 10 microns. This abrasive is also said to be effective in desensitizing hypersensitive teeth. Other patents also referring to the use of particulate hydroxyapatite as a component of a dentifrice composition are US-A-4 342 741 (Aoki), US-A-4 327 079 (Aoki) and US-A-4 634 589 (Scheller).

Although the above-mentioned patents mention many compounds that may also be present as ingredients of the respective compositions described in the patents, no reference is made in any of them to a fluoride. This is not surprising since it would be expected that a fluoride would interact with hydroxyapatite since, after all, the fluoride in a toothpaste is intended to react with the hydroxyapatite of which the tooth enamel is composed during use of the respective dentifrice.

SUMMARY OF THE INVENTION

We have now discovered that dentifrices can be formulated comprising particulate hydroxyapatite and a fluorine-containing anti-caries agent, particularly sodium fluoride or sodium monofluorophosphate in which these ingredients are compatible to a surprising extent. Although there is some loss of available fluoride on storage this is commercially acceptable. Such dentifrices are particularly suitable for combating dental caries.

The hydroxyapatite abrasive is used in a particle size giving satisfactory cleaning without being harmful to the tooth surface when used in appropriate amounts in dentifrices of the invention.

DETAILED DESCRIPTION

The amount of the hydroxyapatite present in oral compositions of this invention will range from 1-50%, usually from about 2% to about 20%, preferably 3 to 15%, by weight of the oral composition. It desirably has an average particle size of from about 1 to about 15 microns, usually from 2-10 and preferably 3 to 10 microns.

Preferred particulate hydroxyapatites for use in sodium monofluorophosphate-containing dentifrices of this invention are synthetic hydroxyapatites of high purity consisting of at least 92% of $Ca_{10}(PO_4)_6(OH)_2$. The remainder will comprise mainly bound water (typically 6% maximum) and a minor amount of calcium carbonate (typically 2% maximum) A process for the preparation of hydroxyapatites is described in GB-A-1 586 915 (British Charcoals & Macdonalds).

A highly pure synthetic hydroxyapatite available commercially is that sold under the trade name CAPTAL by British Charcoals & Maodonalds of Greenock Scotland. This contains about 97% $Ca_{10}(PO_4)_6(OH)_2$. The remaining 3% is mostly bound water with approximately 0 3% calcium carbonate.

The sodium monofluorophosphate will generally be present in the dentifrices of this invention in at amount sufficient to provide from about 50ppm to about 5000ppm F, especially from 200ppm to 1500ppm and more especially from 500ppm to 1500ppm.

The oral composition of this invention will, of course, also contain other ingredients commonly used to formulate such products, depending on the form of the oral product. For instance, in the case of an oral product in the form of a dentifrice cream or paste the product will comprise an humectant-containing liquid phase and a binder or thickener which acts to maintain the particulate solid abrasive in stable suspension in the liquid phase. A surfactant and a flavouring agent are also usual ingredients of commercially acceptable dentifrices.

Humectants commonly used are glycerol and sorbitol syrup (usually comprising an approximately 70% solution). However, other humectants are known to those in the art including propylene glycol, lactitol, and hydrogenated corn syrup. The amount of humectant will generally range from about 10 to 85% by weight of the dentifrice. The liquid phase can be aqueous or nonaqueous.

Likewise numerous binding or thickening agents have been indicated for use in dentifrices, preferred ones being sodium carboxymethylcellulose and xanthan gum. Others include natural gum binders such as gum tragacanth, gum karaya and gum arabic, Irish moss, alginates and carrageenans. Silica thickening agents include the silica aerogels and various precipitated silicas. Mixtures of binders may be used. The amount of binder included in a dentifrice is generally between 0.1 and 10% by weight.

It is usual to include a surfactant in a dentifrice and again the literature discloses a wide variety of suitable materials. Surfactants which have found wide use in practice are sodium lauryl sulphate, sodium dodecylbenzene sulphonate and sodium lauroylsarcosinate. Other anionic surfactants may be used as well as other types such cationic, amphoteric and non-ionic surfactants. Surfactants are usually present in an amount of from 0.5 to 5% by weight of the dentifrice.

Flavours that are usually used in dentifrices are those based on oils of spearmint and peppermint. Examples of other flavouring materials used are menthol, clove, wintergreen, eucalyptus and aniseed. An amount of from 0.1% to 5% by weight is a suitable amount of flavour to incorporate in a dentifrice.

The oral compositions of the invention may also comprise a proportion of a supplementary abrasive agent such as silica, alumina, hydrated alumina, calcium carbonate, anhydrous dicalcium phosphate, dicalcium phosphate dihydrate and water-insoluble sodium metaphosphate.

The oral composition of the invention may include a wide variety of optional ingredients. These include an antiplaque agent such as an antimicrobial compound for example chlorhexidine or 2, 4, 4'-trichloro-2'-hydroxydiphenyl ether, or a zinc salt (see EP-A-161 898); an anti-tartar ingredient such as a condensed phosphate e.g. an alkali metal pyrophosphate, hexametaphosphate or polyphoshate, (see US-A-4 515 772 and US-A-4 627 977) or zinc citrate (see US-A-4 100 269); sweetening agent such as saccharin; an opacifying agent, such as titanium dioxide; a preservative, such as formalin; a colouring agent; or pH controlling agent such as an acid, base or buffer, such as benzoic acid.

For a fuller discussion of the formulation of oral composition reference is made to Harry's Cosmeticology, Seventh Edition, 1982, Edited by J.B. Wilkinson and R.J. Moore, pages 609 to 617.

The invention also relates to a method of combating dental caries which consists in applying to the teeth, such as by brushing, an oral composition according to the invention.

The invention is illustrated by the following Examples of toothpastes containing synthetic hydroxyapatites of high purity as described above. Percentage and parts are by weight.

Example 1

A toothpaste was prepared from the following ingredients.

| Ingredient | % |
|---|---|
| Hydroxyapatite (aps about 9 microns) | 5.00 |
| Silica arogel (Gasil 23) | 10.00 |
| Sorbitol syrup | 40.00 |
| Sodium lauryl sulphate | 1.50 |
| Sodium carboxymethylcellulose | 1.00 |
| Sodium monofluorophosphate | 0.76 |
| Sodium saccharin | 0.20 |
| Titanium dioxide | 1.00 |
| Formalin | 0.04 |
| Flavour | 1.00 |
| Water | to 100.00 |

Example 2

A toothpaste was prepared as in Example 1 save that there was used 10% of an hydroxyapatite having an average particle size of about 3 microns.

The stability of the above toothpastes was evaluated by determining water extractable fluoride (WEF) values. These values were obtained by mixing the toothpaste with water (1 part toothpaste and 9 parts water), centrifuging and then analyzing the supernatant for fluoride by gas liquid chromatography.

The following Table shows 6 month storage stability data at various temperatures for the toothpastes of Examples 1 and 2 which both had an initial fluoride content of 1000 ppm.

TABLE

| Toothpaste | Temp (°C.) | WEF (ppm) |
|---|---|---|
| Example 1 | 6 | 1058 |
|  | 20 | 951 |
|  | 37 | 737 |
| Example 2 | 6 | 957 |
|  | 20 | 898 |
|  | 37 | 647 |

The data show that the two toothpastes had good fluoride stability.

Examples 3 to 8
Toothpastes are made from the ingredients indicated below.

| Ingredient | % Example: 3 | 4 | 5 | 6 | 7 | 8 |
|---|---|---|---|---|---|---|
| Hydroxyapatite | 5.0 | 5.0 | 5.0 | 5.0 | 5.0 | 5.0 |
| Thickening silica | 10.0 | 10.0 | 10.0 | 10.0 | 10.0 | 10.0 |
| Sorbitol syrup (70% solution) | 40.0 | 40.0 | 40.0 | 40.0 | 40.0 | 40.0 |
| Sodium lauryl sulphate | 1.5 | 1.5 | 1.5 | 1.5 | — | — |
| Nonionic detergent (Pluronic F-108) | — | — | — | — | — | 1.5 |
| Sodium carboxymethylcellulose | 1.0 | 1.0 | 1.0 | 1.0 | 1.0 | 1.0 |
| Sodium monofluorophosphate | 0.8 | 0.8 | 0.8 | 0.8 | 0.8 | 0.8 |
| Calcium glycerophosphate | 0.2 | — | — | — | — | — |
| Tetrasodium pyrophosphate | — | 1.5 | — | — | — | — |
| Tetrapotassium pyrophosphate | — | 4.5 | — | — | — | — |
| Triclosan | — | — | 0.2 | 0.2 | — | — |
| Polyethyleneglycol 300 | — | — | 6.0 | — | — | — |
| Zinc citrate trihydrate | — | — | — | 0.5 | 0.5 | 0.5 |
| Chlorhexedine digluconate | — | — | — | — | 0.1 | 0.1 |
| Sodium saccharin | 0.2 | 0.2 | 0.2 | 0.2 | 0.2 | 0.2 |
| Titanium dioxide | 1.0 | 1.0 | 1.0 | 1.0 | 1.0 | 1.0 |

-continued

Examples 3 to 8
Toothpastes are made from the ingredients indicated below.

| Ingredient | % Example: | | | | | |
|---|---|---|---|---|---|---|
| | 3 | 4 | 5 | 6 | 7 | 8 |
| Formalin | 0.04 | 0.04 | 0.04 | 0.04 | 0.04 | 0.04 |
| Flavour | 1.0 | 1.0 | 1.0 | 1.0 | 1.0 | 1.0 |
| Water | to 100.0 | to 100.0 | to 100.0 | to 100.0 | to 100.0 | to 100.0 |

What is claimed is:

1. An oral composition in the form of an aqueous toothpaste for combating dental caries, comprising from about 50 to about 5,000 ppm of a fluoride-containing anti-caries agent selected from the group consisting of sodium fluoride and sodium monofluorophosphate, and from about 1–50% by weight of a particulate abrasive material, wherein the particulate abrasive material comprises hydroxyapatite.

2. A composition according to claim 1, wherein the hydroxyapatite has an average particle size of from 1 to 15 microns.

3. A composition according to claim 1, wherein the hydroxyapatite is a synthetic hydroxyapatite which consists for at least 92% by weight of $Ca_{10}(PO_4)(OH)_2$.

4. A composition according to claim 1, wherein the hydroxyapatite is present in the oral composition in an amount of 1–10% by weight.

* * * * *